United States Patent [19]  
Hoff et al.

[11] 4,003,988  
[45] Jan. 18, 1977

[54] DIRECT AGGLUTINATION TEST FOR PREGNANCY

[75] Inventors: Gail Hoff, Millington; Metka Prevorsek, Morristown, both of N.J.

[73] Assignee: Warner-Lambert Company, Morris Plains, N.J.

[22] Filed: June 1, 1976

[21] Appl. No.: 691,915

[52] U.S. Cl. .............................. 424/12; 23/230 B; 23/253 TP; 252/408
[51] Int. Cl.² ................. G01N 31/02; G01N 33/16
[58] Field of Search ................. 23/230 B, 253 TP; 424/12; 252/408

[56] References Cited

UNITED STATES PATENTS

| 3,088,875 | 5/1963 | Fisk | 424/12 |
|---|---|---|---|
| 3,171,783 | 3/1965 | Fisk | 424/12 |
| 3,234,096 | 2/1966 | Pollack | 424/12 |
| 3,236,732 | 2/1966 | Arquilla | 424/12 X |
| 3,309,275 | 3/1967 | Treacy | 424/12 |
| 3,551,555 | 12/1970 | Schuurs | 424/12 |
| 3,565,987 | 2/1971 | Schuurs | 424/12 |
| 3,862,302 | 1/1975 | Price | 424/12 |

Primary Examiner—Morris O. Wolk  
Assistant Examiner—Sidney Marantz  
Attorney, Agent, or Firm—Albert H. Graddis; Frank S. Chow; George M. Yahwak

[57] ABSTRACT

Direct agglutination reagent for pregnancy testing which comprises the use of suspensions of polystyrene latex particles sensitized with a globulin fraction of anti-serum to human chorionic gonadotropin (HCG). When mixed with urine or blood serum samples containing HCG, this reagent agglutinates indicating a positive test for pregnancy.

9 Claims, No Drawings

DIRECT AGGLUTINATION TEST FOR PREGNANCY

Direct agglutination tests which form the basis of the present invention are well known as to the theory by which they work. U.S. Pat. No. 3,171,783 to Fisk describes such diagnostic tests but states that they are not suggested for use because of a lack of sensitivity.

The present invention has solved many of the difficulties described in the prior art. When the test for pregnancy by direct agglutination is performed using the methods and materials set forth, it results in the realization of the simplicity and accuracy suggested by classic agglutination methods. Furthermore, the test of this invention, when used with the reagent and method disclosed, is 100 to 600% more sensitive than the direct agglutination tests of the prior art which are commercially available. Also, by utilizing the specific buffering system disclosed as part of the reagent system, it was unexpectedly found that false positive reactions would be minimized.

It has been found that the determination of pregnancy can be quickly and accurately made with the simplest equipment by means of the present invention.

Human chorionic gonadotropin (HCG) is present in the blood and urine of pregnant women. This hormone is generated during the formation of the fetus and reaches its highest level about the 50th to 90th day after the first day of the last menstrual cycle. Detectability of HCG as a positive indication of pregnancy is possible from about the 40th day using the present invention.

This is an improved method for determining pregnancy by a simple agglutination of a suspension of polystyrene latex particles having a particle size in the range of 0.15 to 0.9 microns, preferably 0.36 microns, which has been sensitized with a globulin fraction of anti-serum to HCG by incubating the latex with said serum globulin in water for about two hours and then adding an equal volume of a slightly acid solution buffered to pH 6.4 using a 0.5M piperazine dihydrochloride-NaOH buffer containing from 0.0025 to 0.1M, preferably 0.02M glycine, 6% NaCl and 1 part merthiolate per 5,000 parts of buffer mixture. The glycine may be substituted for by glycylglycine in like amounts.

Several suggestions have been made in the prior art concerning direct agglutination tests for determining pregnancy, but generally they have been misnamed. The earlier cited Fisk patent involves the use of HCG anti-serum impregnated agar plates. In the Fisk procedure, an unknown urine sample is concentrated by adsorption on kaolin, and possible HCG is eluted and following known agar well techniques, the test is developed on an agar plate over a four hour period. Another test described as simple and rapid is set forth in U.S. Pat. No. 3,309,275 granted to Treacy. This patent teaches sensitizing a latex with HCG by heating the latex mixed with HCG for a period of four to six weeks. Any HCG present in a urine sample when mixed with known amounts to HCG anti-serum would neutralize the anti-HCG if the person who provided the sample were pregnant. The Treacy test is then run and in the case of pregnancy, agglutination of the latex would not occur.

EXAMPLE I

Rabbit Anti-Human Chorionic Gonadotropin Globulin

A quantity of blood is withdrawn from rabbits which were presensitized to HCG. The blood is allowed to clot at room temperture at which time the serum is removed from the clot and cooled to 4° C. All reagents used in the preparation have also been cooled to 4° C.

The serum is fractionated by the addition of a saturated ammonium sulfate solution in an amount which will yield a 40% solution of ammonium sulfate after the addition has been made. The precipitate which forms when the ammonium sulfate is added contains anti-HCG and is collected by filtration, centrifugation, or other means, and the supernatant is discarded. The precipitate is resuspended in a wash solution of 40% saturated ammonium sulfate to remove all traces of the supernatant contaminates. The precipitate is again collected and dissolved in a 0.85% by weight sodium chloride solution in an amount which will yield an anti-HCG concentration of about 40% of its original concentration in whole serum. This solution is further refined by dialyzing it against an 0.85% sodium chloride solution. The dialysate so obtained may be used immediately or frozed at −20° C for future use.

EXAMPLE II

2% Polystyrene Latex Suspension

Polystyrene latex particles having a particle size of between about 0.15 to 0.9 microns, are suspended in a sufficient amount of distilled water to obtain the desired concentration. Although not necessary, it is advantageous that the concentration be confirmed by colorimetric standarization.

EXAMPLE III

Anti-HCG-Latex Reagent 25 cc of a piperazine dihydrochloride buffer at pH 6.4 containing 0.02M aminoacetic acid, 6% sodium chloride, and 1:5000 to 1:15000 merthiolate (thimerosal) is added to 25 cc of distilled water and heated to 50° C. 50 cc of the latex suspension prepared according to Example II is rapidly added to about 8 cc of anti-HCG globulin prepared according to Example I and the mixture incubated at 56° C for about two hours. After incubation sucrose in an amount of about 0.5% to about 20%, preferably about 1 to about 3%, and bovine serum albumin in an amount of about 0.1% to about 20%, preferably about 0.1 to about 1.0%, are added to the reagent. After thorough mixing the reagent is cooled and stored at 4° C. The reagent so prepared is stable for up to three years at 4° C.

The saturated ammonium sulfate which precipitates the antiserum to HCG (Example I) may be added in amounts such that its resulting concentration in combination with the serum is between 33 and 60% saturated, preferably between 40 and 50% saturated.

The 56° temperature at which the latex is incubated (Example III) is preferred, but not critical and may be varied on either side with adjustments made in the duration of the incubation, i.e. lengthening it for lower temperatures and shortening it for higher ones.

The amount of anti-HCG added to the latex (Example III) is controlled so that the particles are just completely coated. This eliminates the need for repeated washing necessary to remove any excess unadsorbed globulin from the reagent.

The buffer system (Example III) utilized in the reagent system allows the reagent to be used with serum specimens, as well as in conventional urine testing. Furthermore, it minimizes false positive reactions due to the Rheumatoid factor in sera. Lastly, it also allows the pregnancy test to be run on urine samples containing range quantities of blood or protein.

The addition of the sucrose in bovine serum albumin (Example III) was found not only to make a better preparation for distinguishing positive from negative reactions, but it also allows the reagent to be placed on cards and dried, thus providing even longer stability of reagents at room temperature.

EXAMPLE IV

Dried Test Cards

50 Lamda of the reagent suspension made in accordance with Example III is dispensed onto disposable slides which may be glass, plastic, cardboard, or other material. This reagent is allowed to dry on the slides at room temperature at which time it is ready for use in the pregnancy test procedure outlined in Example V.

EXAMPLE V

Pregnancy Test Procedure

Urine is collected from the patient and filtered to remove contaminating material. The filtration is preferably accomplished using a device of U.S. Pat. No. 3,698,556, however, other filtration means may be used to filter the sample as well.

A drop of filtered urine is placed on a clear glass slide and mixed with one drop of the latex reagent prepared according to Example III. The slide is rocked slightly back and forth for about two minutes. If the urine sample contains HCG, discreet particles or clumps of latex easily discernible to the eye are formed; if the urine did not contain HCG the latex continues to appear as a uniform suspension.

Serum may, of course, be used in the above procedure in lieu of the filtered urine. The drop of urine or serum may also be placed on the test cards made according to Example IV in lieu of the clear glass slide, thereby avoiding the necessity of adding a drop of the latex reagent.

Tests of 215 pregnant and 414 non-pregnant women were performed on urine samples using the materials and method of the present invention. Time proved the results obtained to be 99.3% accurate.

The reagent and test system was also found (Example VI) to be sensitive to as little as about 1.0 IU or HCG per ml of urine.

EXAMPLE VI

Comparison To Commercial Pregnancy Tests

Thirteen commercial pregnancy tests were evaluated for sensitivity using known quantities of human chorionic gonadotrophin (HCG) dissolved in urine from a non-pregnant female. Seven were based on the principle of latex agglutination inhibition (indirect slide tests), one was a tube test using the same principle, three were based on the principle of passive hemagglutination inhibition (HAI) and three, including our test were based on a direct agglutination of latex.

Human chorionic gonadotrophin (HCG): Preparation A Without Urine, Division Biological Standards, National Institute of Health, Bethesda, Maryland. The contents of one vial containing 5000 i.u. HCG were dissolved in 5 ml distilled water to give a concentration of 1000 i.u./ml. Further dilutions were made in duplicate in filtered urines from non-pregnant women to concentrations ranging from 10 i.u./ml through 0.6 i.u./ml. In this way, known concentrations of HCG were contained in different levels.

Urine from non-pregnant women was collected and filtered through Whatman 42 and DE81 paper. An aliquot of each was saved as a "negative" control for the pregnancy tests and the remainder was used to prepare dilutions of HCG.

As shown in Table I, the sensitivity found using the NIH standard for HCG ranged from 0.6 I.U./ml through 5 I.U.ml.

Table 1

| | Sensitivity of Pregnancy Tests | | |
|---|---|---|---|
| Name | Type | Sensitivity Claim (i.u./ml) | Sensitivity Found (i.u./ml) |
| A | LDS[1] | not stated | 3 – 4 |
| B | LIS[2] | 1.5 – 2.5 | 2.5 – 5 |
| C | LIS | 2 | 2.5 – 5 |
| D | LIS | 3 | 2.5 – 5 |
| E | LIS | 3.5 | 2.5 – 5 |
| F | LIS | 1 – 2 | 1.25 – 2.5 |
| G | LIS | 1 – 2 | 1.25 – 2.5 |
| H | LIT[3] | 1 | <0.6 |
| I | LDS | 2 | 1.25 – 2.5 |
| According To This Invention | LDS | 1 | 0.6 – 1.25 |
| J | HAI[4] | 0.75 | 0.6 – 1.25 |
| K | HAI | 0.75 | <0.6 |
| L | HAI | 1 | <0.6 |

[1]Latex direct slide test
[2]Latex indirect slide test
[3]Latex indirect tube test
[4]Hemagglutination inhibition (tube test)

While the preferred embodiment of the invention has been described herein, it is to be understood that various changes and modifications may be made without departing from the spirit and scope of the invention as defined by the appended claims.

We claim:

1. A liquid reagent having the characteristics of agglutination when placed in contact with fluids which contain human chorionic gonadotropin and which comprises a polymeric latex carrier having a particle size between about 0.15 to about 0.9 microns, said carrier being coated with rabbit anti-human chorionic gonadotropin serum and the reagent being buffered to a pH of from 5.0 to about 8.6 with a buffer which comprises about 0.005 to about 1.0M piperazine dihydrochloride, water and sufficient sodium hydroxide to obtain the buffered pH.

2. The reagent set forth in claim 1 wherein the carrier is a polystyrene latex having a particle size of about 0.36 microns, wherein the pH is 6.4, and which further comprises about 0.0025 to about 0.1M aminoacetic acid, about 1 to about 10% sodium chloride, and about 1 part of merthiolate per 5,000 parts of the reagent.

3. The reagent as set forth in claim 2 wherein the reagent contains 0.5M piperazine dihydrochloride-sodium hydroxide buffer, 0.02M aminoacetic acid, and 6% sodium chloride.

4. The reagent as set forth in claim 2 which further comprises about 2% sucrose and about 0.5% bovine serum albumin.

5. A liquid reagent having the characteristics of agglutination when placed in contact with fluids containing human chorionic gonadotropin and comprising a buffering system containing polymeric latex particles of about 0.15 to about 0.9 microns coated with anti-human chorionic gonadotropin serum, the improvement of said reagent comprising the buffering system consisting of piperazine dihydrochloride, sodium hydroxide, aminoacetic acid, sodium chloride, merthiolate, and water and having a pH of about 5 to about 8.6.

6. The reagent as set forth in claim 5 wherein a further improvement comprises said reagent further comprising about 0.5% to about 20% sucrose and about 0.1 to about 20% bovine serum albumin.

7. The reagent as set forth in claim 6 which comprises about 2% sucrose and about 0.5% bovine serum albumin.

8. A method for preparing a reagent which agglutinates when contacted with fluids containing human chorionic gonadotropin which comprises:
  injecting a quantity of human chorionic gonadotropin into a rabbit and allowing the rabbit to produce antibodies to the chorionic gonadotropin;
  withdrawing a portion of said rabbit's blood and allowing the blood to undergo normal clotting reactions;
  separating the serum from the clot,
  precipitating the globulin portion of said serum by the addition of about a 35 to 60% ammonium sulfate solution;
  purifying the precipitate to remove all traces of supernatant contaminants;
  dissolving the precipitate in a normal saline solution;
  mixing the globulin solution so obtained with polystyrene latex particles having a size of between about 0.15 to 0.9 microns;
  incubating said mixture at about 56°;
  adding an amount of from 0.005 to 1M piperazine dihydrochloride buffer having a pH of from 5.0 to 8.6 and containing 0.0025 to 0.1M aminoacetic acid and 1 to 10% by weight of sodium chloride;
  incubating said mixture for an additional time; and
  adding sucrose to said mixture in an amount of about 0.5% to about 20% and bovine serum albumin in an amount of 0.1% to about 20%.

9. The method of claim 8 which further comprises adding an amount of reagents so prepared to a disposable slide; and drying the reagent on said slide.

* * * * *